United States Patent [19]

Collins

[11] Patent Number: 5,371,463

[45] Date of Patent: Dec. 6, 1994

[54] MAGNETIC INSTRUMENT FOR DETECTING A POOR BAND BETWEEN A MAGNETIC LAYER AND A NON-MAGNETIC SUBSTRATE

[76] Inventor: Richard M. Collins, 38 Lodge La., E. Setauket, N.Y. 11733

[21] Appl. No.: 945,707

[22] Filed: Sep. 16, 1992

[51] Int. Cl.[5] .................... G01N 27/72; G01R 33/12
[52] U.S. Cl. ................................ 324/228; 324/262
[58] Field of Search ............... 324/228, 229, 230, 231, 324/262, 207.26; 73/150 R, 150 A

[56] References Cited

U.S. PATENT DOCUMENTS 4,634,974  1/1987  Hunter ..................... 324/228

*Primary Examiner*—Walter E. Snow
*Attorney, Agent, or Firm*—Pollock Vande Sande & Priddy

[57] ABSTRACT

A laminated structure may be tested for weak joints by passing a magnet over the surface. If the outer surface is of a magnetic material, weak bonding forces will be overcome by the magnet which causes deflection of the magnetic layer, relative to a non-magnetic substrate. The deflection is sensed and signifies the detection of a weak bond area. The testing procedure is accomplished without destructively testing a structure.

5 Claims, 2 Drawing Sheets

MAGNETIC INSTRUMENT FOR DETECTING A POOR BAND BETWEEN A MAGNETIC LAYER AND A NON-MAGNETIC SUBSTRATE

FIELD OF THE INVENTION

The present invention relates to nondestructive testing techniques, and more particularly to a portable apparatus using magnetically induced laminate separation for detecting weak spots. Large laminated structures often have localized joint weakness at the interface between layers where adhesive has been applied. Problems are particularly troublesome in the aircraft industry where delamination of aircraft skin layers or protective layers can lead to serious results.

BACKGROUND OF THE INVENTION

There is no end item nondestructive test which will verify actual localized attachment joint strength. Current nondestructive inspection such as ultrasonic flaw detection, ultrasonic resonance, and eddy sonic methods are capable of detecting voids (areas of zero adhesion) and some strength conditions relatable to the cohesive properties of the joining material but not to adhesion properties at the joint interface. This results in undetectable weak adhesion conditions commonly known as kissing bonds and grazing bonds. Present manufacturing technology practice is to accept the bond adhesion strength based on process control methods such as: raw material control, cleaning and pretreatment of substrates, interface dimensional fit, cure cycle time-temperature and pressure controls, destructive evaluation of representative coupons, and destructive test of actual structure. The present method of detecting weak adhesion bondlines is for in-service failure to occur or to perform a destructive analysis of structure suspected of weak joints. This results in extensive repairs or scrap structure. Improved nondestructive testing apparatus and methods must be developed to allow inspection to verify the existence of attachment strength.

BRIEF DESCRIPTION OF THE PRESENT INVENTION

The basic principle of the present invention is the utilization of magnetic force, applied to an external magnetic layer to induce separation between the magnetic layer and a non-magnetic substrate and detecting the occurrence of such separation. The separation may be magnetically induced with low magnetic forces where an adhesive interface bond between the magnetic and non-magnetic layers is weak to begin with. Alternatively, a variably increasing magnetic force may be applied until an otherwise satisfactory bond is broken thereby allowing investigators to determine the strength of the bond in the first place. Accordingly, there are three major embodiments of the present invention which enable alternative gauges to perform the following functions:

1. nondestructively evaluating and inspecting the joining strength of a magnetic coating or magnetic layer of pre-cast material which is adhesively bonded to a non-magnetic substrate;
2. nondestructively evaluating the total attachment strength of two materials joined together by adhesion or other means;
3. calibration of nondestructive inspection systems based on surface strain measurements such as laser shearography, holography, etc.

In each of these examples, a magnet applies a tension load perpendicular to an attachment interface joint. It is the magnet which induces displacement of an outer magnetic coating joint so that an appropriate type of sensor may detect surface deflection indicative of bond-line strain or failure.

Accordingly, the present invention offers method and apparatus for accomplishing non-destructive evaluation of a bonded joint which is extremely useful for the aviation and laminating industries.

The invention described herein applies a constant flatwise tension load upon the joint while scanning (inspecting) along the joint. Where weak adhesion exists, the joint will be broken and deflection will occur in a manner previously undetectable without destructive testing. The present invention does not attempt to measure cohesive or adhesive strengths individually, but does relate to total strength of the attachment joint.

Accordingly, it is a primary object of the present invention to provide a gauge or instrument capable of applying a controlled fixed or variable flatwise tensile or peel load upon the structure joint (attachment interface) and to measure the resulting surface deflection. If the bondline attachment strength is greater than the force applied by a magnet, zero deflection occurs. The logical conclusion is therefore that joint strength is greater than the magnetically induced force. However, if the joint strength is weak (less than the force applied by a magnet), then the surface material will be attracted towards the magnet. This deflection will be detected by an appropriate sensor which may include a mechanical dial indicator, eddy current coil, displacement transducer, strain gauge, etc. Of course, any area of a joint that is unbonded or void would also be detected.

The primary use of the invention would be to inspect a joint containing an outer magnetic layer joined to a non-magnetic substrate, such as magnetic rubber adhesively bonded or sprayed onto an aluminum, titanium, or other non-magnetic substrate material. This magnetic sprayable or cast material treatment is commonly attached to the exterior surface of a metal airframe structure for the purpose of altering the electro-magnetic signature of the aircraft. In some cases the invention would be used to detect void areas in the joint interface between relatively thick magnetic material (commonly identified as bi-layer) and the non-magnetic substrate. These thicker materials are difficult or impossible to inspect by alternate nondestructive testing methods such as ultrasonics or eddy sonics.

BRIEF DESCRIPTION OF THE FIGURES

The above-mentioned objects and advantages of the present invention will be more clearly understood when considered in conjunction with the accompanying drawings, in which.

DETAILED DESCRIPTION OF THE INVENTION

Figure 1A:
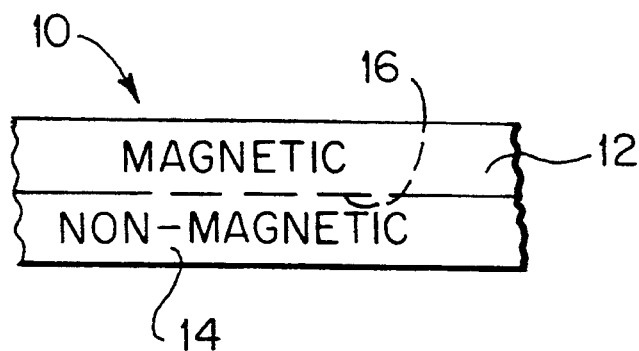
FIG. 1A is a diagrammatic view of a laminate including an outer magnetic layer and an inner non-magnetic layer.

Referring to the figures, and more particularly FIG. 1A, reference numeral 10 indicates a simple two-layer laminate which includes an outer magnetic layer 12 adhesively bonded to a non-magnetic layer 14. As previously explained, the problem solved by the present invention is the detection of weak bonding points in the interface joint 16 between layers 12 and 14.

Figure 1B:
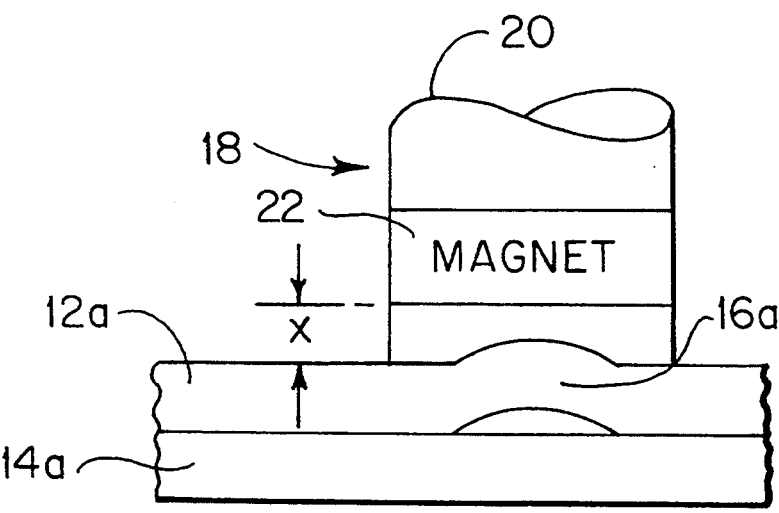
FIG. 1B is a diagrammatic view of the laminate shown in FIG. 1A and a magnetic member riding on the surface of the magnetic layer inducing a deflection thereof in the region of a weak adhesive bond between the layers.

FIG. 1B schematically illustrates the severance of the weak bond when a magnet applies a magnetic force to the magnetic layer 12a causing a rupture of the weak bond and deflection of the magnetic layer relative to the non-magnetic substrate 14a. In its most simple form, a magnetic assembly is generally indicated by reference numeral 18 and is seen to include a magnet 22 enclosed within a housing 20 which normally spaces the magnet 22 from the surface of magnetic layer 12a. This is represented by the distance x illustrated in FIG. 1B. However, when the magnetic assembly 18 encounters a weak adhesive joint, it displaces the magnetic layer 12a relative to the non-magnetic layer 14a, the deflection being indicated by 16a in FIG. 1B. This decreases the distance x which is detectable by conventional methods.

Figure 2:
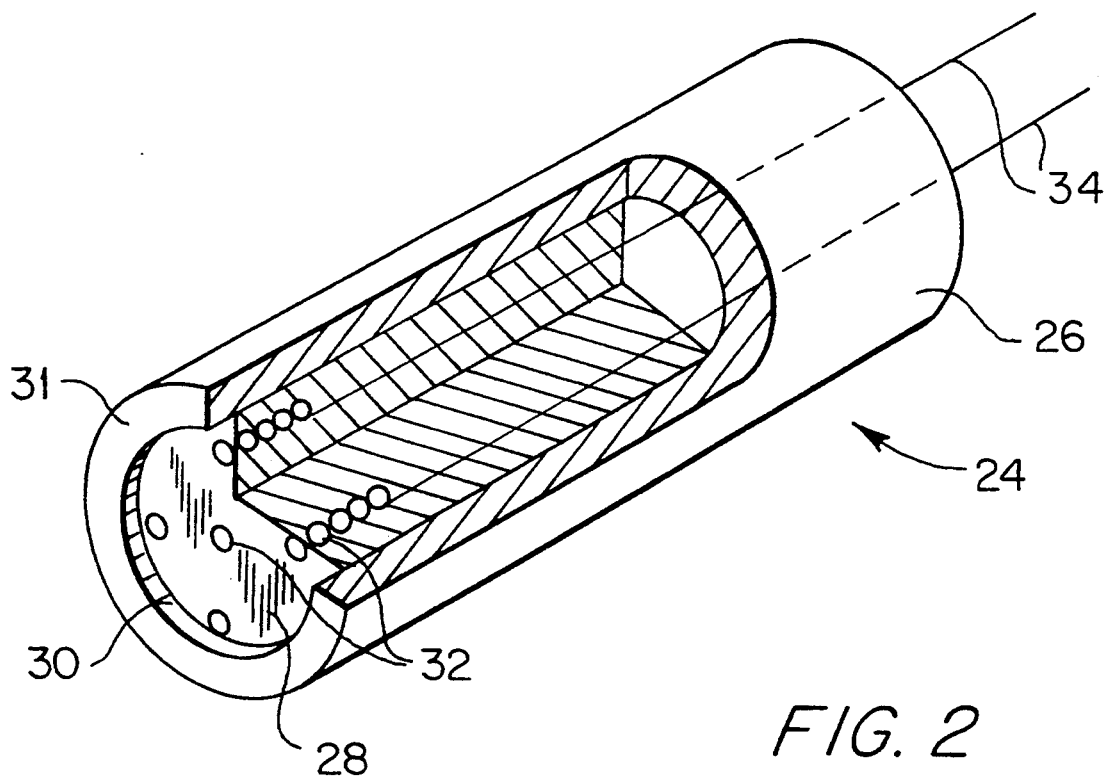
FIG. 2 is a diagrammatic sectional view of a magnetic member as employed in one embodiment of the present invention.

FIG. 2 illustrates an embodiment of the present invention for achieving simultaneous magnetic attraction and detection by means of eddy current generation. The assembly is generally indicated by reference numeral 24 and is seen to include a tubular housing 26 coaxially enclosing a cylindrically shaped magnet 28. The outer end of magnet 28 is recessed from the corresponding outer end of tubular member 26, as indicated by reference numeral 30. A number of longitudinally extending eddy current coils 32 are embedded within the magnet 28. AC excitation is provided the eddy currents through wires 34; and as the assembly is passed over a weak adhesive bond area causing deflection, eddy current changes will be detected as a result of the variation in distance x (FIG. 1B). The actual eddy current detectors are not shown nor described since they are well known to those of ordinary skill in the art. It should be mentioned that, although a permanent magnet 28 is indicated in FIG. 2, an electromagnet may be used as well.

Figure 3:
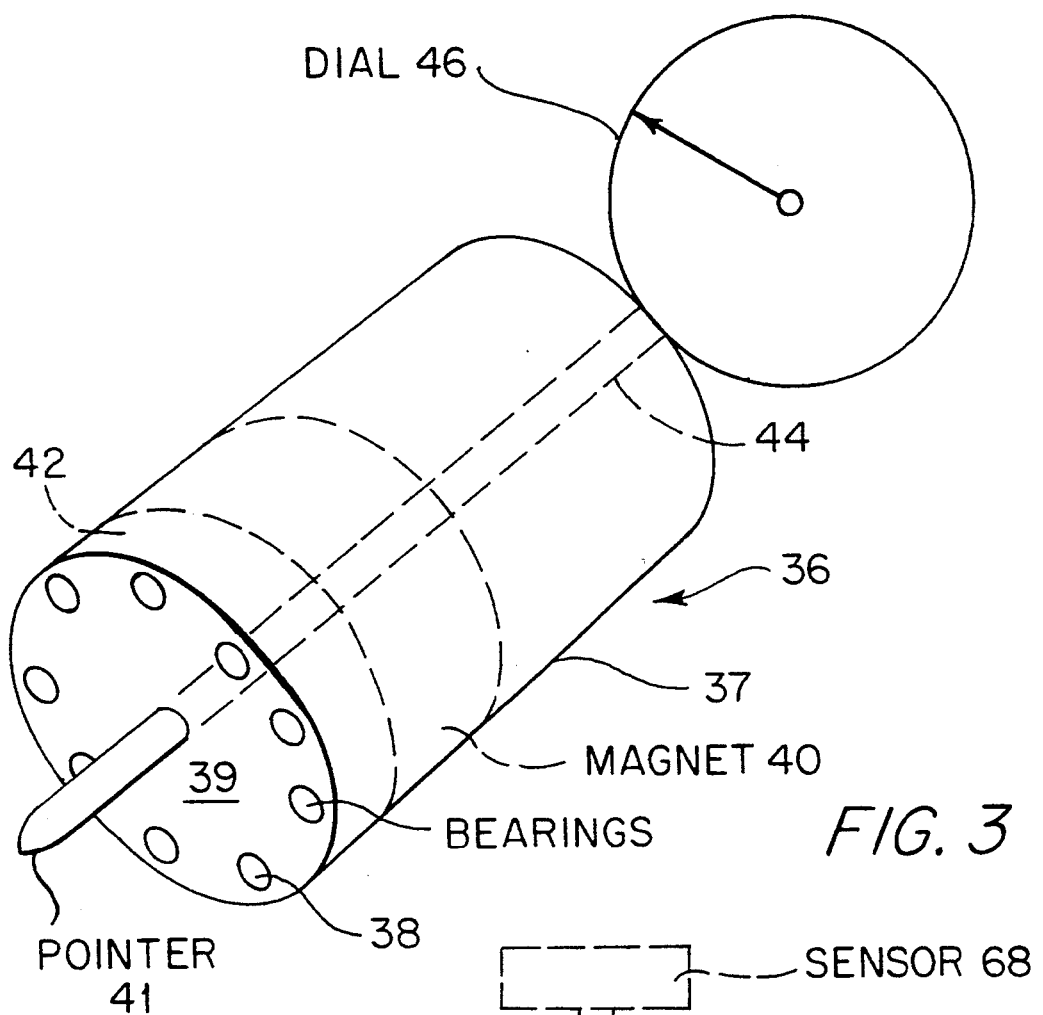
FIG. 3 is a schematic perspective view of a second embodiment of the present invention.

A further embodiment of the present invention is diagrammatically indicated in FIG. 3 wherein a mechanical deflection detector is employed. The assembly for this embodiment is generally indicated by reference numeral 36 and is seen to be enclosed within a cylindrical body 37. Specifically, a lower housing end has ball bearings 38 mounted thereto so as to allow rolling motion of the assembly over a laminate structure. An annular magnet 40 is coaxially spaced from the bottom end so as to create the air gap or distance x (FIG. 1B). It is the magnet 40 which induces deflecting forces upon a magnetic layer that is weakly bonded to a non-magnetic substrate. The deflection is monitored by a spring-loaded pointer 41 which is linked to a dial 46 in a manner similar to conventional mechanical dimension gauges.

In operation of the device shown in FIG. 3, normal passage across a well-bonded laminate will register a constant dial reading. However, if the assembly passes over a weak adhesive joint, deflection will be magnetically induced by magnet 40 and the dial 46 will present a different reading. This indicates that the assembly 36 is physically located over a weak adhesive bond.

In connection with the examples of FIGS. 2 and 3, the magnetic layer deflects toward the magnet by an amount which depends upon the localized stiffness (elastic modulus) of the deflecting layer. The choice of selected sensor depends upon the expected material deflection dimension.

Figure 4:
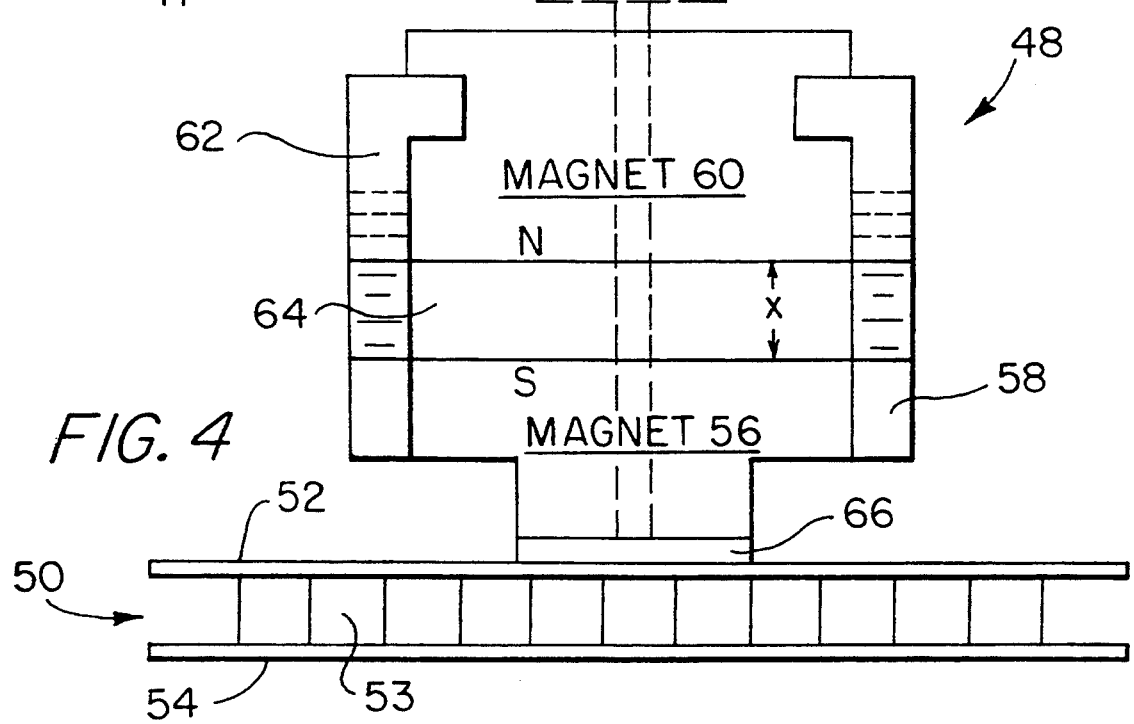
FIG. 4 is a diagrammatic view of a third embodiment of the present invention.

FIG. 4 illustrates a further embodiment of the present invention which has particular utility in establishing the strength of an adhesive bond between two layers. For example, FIG. 4 illustrates a honeycomb laminated structure generally indicated by reference numeral 50 which, for example, may include a titanium layer 52, intermediate honeycomb layer 53, and an internal support layer 54. The indicated assembly 48, in accordance with the present invention, incorporates a lower annular magnet 56 which is adhesively bonded to the outer layer 52 by means of a suitable adhesive 66 which is stronger than the adhesive employed between the various layers of laminate 50. The main purpose of the assembly illustrated in FIG. 4 is to determine the strength of the physical bond between the layers of laminate 50 by variably increasing the magnetic force of a second magnet 60 coaxially displaced from the lower magnet 56. When the magnetic attraction of magnet 56 to magnet 60 is greater than the adhesive force between layers of laminate 50, delamination occurs at a value that can be measured. The variation in magnetic field is accomplished by mounting magnets 56 and 60 in their respective collars 58 and 62. By screwing down collar 62, the air gap distance x is decreased thereby increasing the magnetically induced load on magnet 56. This, of course, is translated to the upper layer 52 of the laminate due to the fact that the bond of adhesive 66 is stronger than the bonding material used in the laminate 50. When the bond of the laminated structure is overcome, magnet 56 slides up in its collar 58 and use of an appropriate conventional displacement sensor 68 signals this occurrence. Again, it is pointed out that the magnets may be permanent or electromagnets.

The material used at adhesive bond 66 may be a room temperature, high tensile strength contact adhesive which is very low in peel strength and can thus easily be removed (peeled off) at a slightly elevated temperature.

It should be pointed out that the direction and total stress applied to the joint interface can be controlled by careful selection of size, shape, material, and pole orientation of the magnets.

In utilizing the embodiment of FIG. 4, one must predetermine the stiffness of the surface layer. It should be remembered that the stiffer the layer, the less surface deflection will occur per unit area. A selection is made of the appropriate sensor based on the expected surface deflection. Then, one must predetermine the joint loading required to verify bondline (attachment) strength.

In operation of the assembly 48 of FIG. 4, it is set on a laminated structure 50 and the air gap dimension x is adjusted by moving the upper indicated magnet 60 closer to the lower magnet 56. Maximum load will be applied when the dimension x is at a minimum distance. The assembly could be pre-calibrated so that various dimensions x would result in a known attraction force between the magnets and thereby at the joint interface. Gradually, the applied force is increased until the predetermined load is obtained and the assembly is then removed. If no surface deflection is observed, the bondline joint strength is greater than the applied force. If deflection is observed, then the joint strength is weaker or bondline failure is indicated. Alternate operation would be as follows: as the joint of the laminated structure is increasingly stressed, mechanical displacement will cause acoustic emissions to propagate within the structure. These acoustic emission signals will be induced at stress levels well below design or ultimate strength. Selection of appropriate acoustic emission equipment will enable estimation of maximum bondline strength while only applying relatively low (safe) stress levels. The assembly 48 may be removed by applying a slightly elevated temperature thereby weakening the bond 66 and permitting the assembly to be peeled off.

The invention as described above would provide a fast, less expensive means of evaluating a structure suspected of weak joints, due to unexpected process variations, or low residual strength due to in-service operations. Presently, structure suspected of weak joint strength is destructively evaluated which requires extensive test preparation and repair, or the suspect structure is scrapped.

Additional uses would be evaluate advanced fiber matrix interlaminar tensile/compression strength, space shuttle tile bondline joints, and residual strength of all types of joints.

An alternate use would be to apply a "localized" controlled force on a structure surface to calibrate lines of force images based on surface strain non-destructive testing methods such as laser shearography or holographic methods. Comparison of images from unstressed structure to images of structure with various degrees of loading would be useful to estimate residual strength of a joint without applying maximum load. The stress images of optimum strength joints will be different than joints with less than optimum strengths.

The embodiment illustrated in FIG. 4 is useful in that it allows the magnetic load to be variably increased. As the attraction forces become stronger, the tension at the bondline increases. Adjustment of the dimension x to a minimum separation between the magnets will result in maximum stressing of the bondline. The force exerted between the magnets and transferred to the bondline at various x dimensions can be calculated or measured by experiment. Surface strain images caused by various dimensions x of optimum strength joints, when compared to images of less than optimum strength joints, would be a means of calibrating the surface strain fringe pattern to residual joint strength. Thus, it is possible to estimate joint strength without applying maximum stress to the joint.

Accordingly, the present invention, when used as described above would provide a fast, less expensive means of evaluating structure suspected of weak joints, due to unexpected process variations, or low residual strength due to in-service operations. Presently, structure suspected of weak joint strength is destructively evaluated which requires extensive test preparation and repair, or the suspect structure is scrapped.

It should be understood that the invention is not limited to the exact details of construction shown and described herein for obvious modifications will occur to persons skilled in the art.

I claim:

1. A portable instrument for measuring the quality of bonding between a non-magnetic substrate and a magnetic overlying layer, the instrument comprising:
   a housing;
   a stationary magnet located in the housing for deflecting an insecurely bonded overlying layer from the non-magnetic substrate when the housing passes across the insecurely bonded overlying layer; and
   means located in the housing for detecting the deflection of the insecurely bonded layer.

2. The instrument set forth in claim 1 wherein the detecting means comprises:
   coils mounted in the magnet for generating induced eddy currents in response to magnetic layer deflection; and
   wire leads connected to the coils for carrying the eddy currents.

3. A portable instrument for measuring the quality of bonding between a non-magnetic substrate and a magnetic overlying layer, the instrument comprising:
   a housing;
   a stationary magnet located in the housing for deflecting an insecurely bonded overlying layer from the non-magnetic substrate when the housing passes across the insecurely bonded overlying layer; and
   means located in the housing for detecting the deflection of the insecurely bonded layer;
   the detecting means having
   (a) a spring-loaded pin coaxially mounted through the magnet for riding along the surface of the overlying layer; and
   (b) a measurement dial connected to the pin for measuring the deflection of the overlying layer.

4. A method for detecting weak adhesion strength between joined overlying magnetic and non magnetic layers comprising the steps:
   subjecting areas of the magnetic layer to a constant localized magnetic field sufficient to deflect an area of weak bonding; and
   sensing deflection of the magnetic layer relative to the non magnetic layer in an area of the localized field thereby confirming an inadequate bond thereat.

5. The method set forth in claim 4 wherein the step of sensing deflection includes:
   the generation of eddy currents in proximity to an overlying magnetic layer; and
   the detection of a variation of eddy currents as the localized field causes deflection in an area.

* * * * *